United States Patent [19]
Sutton et al.

[11] 3,944,571
[45] Mar. 16, 1976

[54] ESTER DERIVATIVES OF PULVINIC ACID

[75] Inventors: Blaine M. Sutton, Hatboro; Donald T. Walz, Drexel Hill; James W. Wilson, Wayne, all of Pa.

[73] Assignee: SmithKline Corporation, Pa.

[22] Filed: May 6, 1974

[21] Appl. No.: 467,367

Related U.S. Application Data

[60] Division of Ser. No. 191,051, Oct. 20, 1971, Pat. No. 3,826,839, which is a continuation-in-part of Ser. No. 94,974, Dec. 3, 1970, abandoned.

[52] U.S. Cl............................ 260/343.6; 260/340.5
[51] Int. Cl.$^2$........................................ C07D 307/28
[58] Field of Search...................... 260/343.6, 340.5

[56] References Cited
UNITED STATES PATENTS

| | | | |
|---|---|---|---|
| 3,676,464 | 7/1972 | Foden et al. | 260/343.6 |
| 3,818,048 | 6/1974 | Foden et al. | 260/343.6 |

OTHER PUBLICATIONS

Bhutani et al., Chem. Abst., 73: 34988a, (1970).
Grover et al., J. Chem. Soc. 1960, pp. 2134–2138.
Klasa, Hoppe–Seyler's Z. Physiol. Chem., 287, pp. 195–204, (1951).
Koller et al., Chem. Abst., 27: 2683 (1933).
Letcher et al., Chem. Abst., 68: 21418m, (1968).
Mittal et al., J. Chem. Soc., 1956 pp. 1734–1735.
Piutti et al., Chem. Abst., 21: 1110, (1925).

*Primary Examiner*—James A. Patten
*Assistant Examiner*—Michael Shippen
*Attorney, Agent, or Firm*—Richard D. Foggio; William H. Edgerton

[57] ABSTRACT

Pharmaceutical compositions having anti-arthritic activity comprising an ester derivative of pulvinic acid and methods of producing anti-arthritic activity by administering internally said compositions. Certain of the pulvinic acid derivatives are novel compounds per se.

5 Claims, No Drawings

ESTER DERIVATIVES OF PULVINIC ACID

This is a division of application Ser. No. 191,051 filed Oct. 20, 1971, now U.S. Pat. No. 3,826,839 which is a continuation-in-part of application Ser. No. 94,974 filed Dec. 3, 1970, now abandoned.

This invention relates to novel pharmaceutical compositions having anti-arthritic activity and to methods of producing anti-arthritic activity by administering said compositions. More specifically, the compositions of this invention comprise an ester derivative of pulvinic acid as the active medicament.

The novel pharmaceutical compositions of this invention, in dosage unit form, comprise a nontoxic pharmaceutical carrier and an ester derivative of pulvinic acid of the following general structural formula:

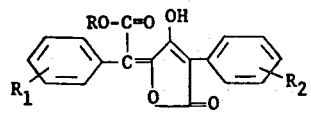

FORMULA I wherein:

R represents methyl or ethyl; and $R_1$ and $R_2$ each represent hydrogen, chlorine, dichloro, bromine, fluorine, methyl, lower alkoxy of from 1 to 4 carbon atoms, dimethoxy, trimethoxy, methylthio, methylsulfinyl, methylenedioxy in adjacent positions, trifluoromethyl or combinations of chlorine, bromine, fluorine, methyl and lower alkoxy of from 1 to 4 carbon atoms. The substituents in the $R_2$ benzene ring are designated by a prime (').

Advantageously the compositions of this invention comprise a compound of formula I above where R is methyl and $R_1$ and $R_2$ are each hydrogen, chlorine, fluorine, methyl, methoxy, methylenedioxy, ethoxy, n-butoxy, methylthio or methylsulfinyl. Preferably R is methyl, $R_1$ is hydrogen and $R_2$ is hydrogen, chlorine, fluorine, methyl, methoxy, methylenedioxy, n-butoxy, methylthio or methylsulfinyl.

The compounds of formula I above are either known or are prepared by the synthetic method outlined as follows:

in which R, $R_1$ and $R_2$ are as defined above for formula I. Thus a phenylacetonitrile is condensed with ethyl oxalate in an alcoholic solution of an alkali metal lower alkoxide, such as sodium methoxide or ethoxide to give the ethyl 3-cyano-3-phenylpyruvate. This compound is further condensed with a phenylacetonitrile in an alcoholic solution of an alkali metal lower alkoxide, such as sodium methoxide or ethoxide to yield the 2,5-diphenyl-3,4-dioxoadiponitrile. The above condensations may also be carried out using a metal hydride, such as sodium hydride, in diglyme. The adiponitrile derivative is refluxed for a short period of time, for example one or two hours, in an aqueous acid solution such as water/glacial acetic acid/concentrated sulfuric acid mixture and the resulting pulvinic acid is refluxed with acetic anhydride to furnish the corresponding pulvinic acid lactone of formula II above. The dilactone is ring opened to the products of formula I by brief refluxing in the appropriate alkanol, that is methanol or ethanol, containing a mineral acid such as hydrochloric acid. Alternatively, the lactone of formula II is ring opened by treatment with methanolic potassium hydroxide at ambient or lower temperature for from 30 minutes to several hours to give the methyl ester products of formula I.

When $R_1$ and $R_2$ are different in the above synthetic sequence, the ring opening of the dilactone of formula II gives a mixture of positional isomers, namely compounds of formula I and compounds of the following formula:

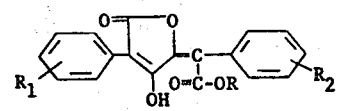

FORMULA III

The ratio of isomers obtained is variable and depends on the nature of $R_1$ and $R_2$. The isomers can be separated by fractional crystallization and/or chromatographic procedures. Their identity is determined from the nuclear magnetic resonance patterns of the aromatic protons. This identification can be confirmed by degradative ozonolysis. A useful modification of standard fractional crystallization procedures is the em-

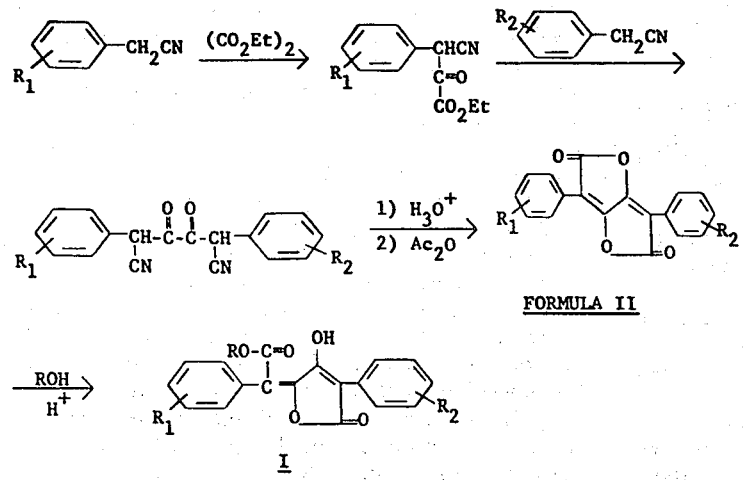

FORMULA II ployment of a base such as an alkali metal alkoxide, for example sodium methoxide, in the recrystallization solvent. More specifically a mixture of isomers obtained as above is dissolved in methanol containing sodium methoxide, cooled to separate one isomer and the filtrate is acidified with for example dilute mineral acid to give the other isomer.

Certain of the compounds of formula I above are novel compounds and as such form a part of this invention. These compounds may be represented by the following formula:

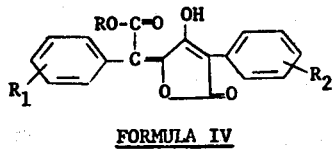

FORMULA IV wherein:
R represents methyl or ethyl; and
$R_1$ and $R_2$ each represent hydrogen, dichloro, n-butyoxy, methylthio, methylsulfinyl, methylenedioxy in adjacent positions or combinations of chlorine, bromine, fluorine, methyl and lower alkoxy of from 1 to 4 carbon atoms, provided that both $R_1$ and $R_2$ are not hydrogen.

The anti-arthritic activity of the compositions of this invention is measured by the ability of the active medicament to inhibit or suppress adjuvant-induced polyarthritis in rats. The active medicaments of formula I produce marked inhibition of the development of adjuvant arthritis in rats at daily oral doses of from 1 mg. to 50 mg. per kilogram of body weight. Adjuvant arthritis in rats is produced by a single injection of 0.75 mg. of Mycobacterium butyricum suspended in white paraffin (N.F.) into a hindpaw (left footpad). The injected paw becomes inflamed and reaches a maximum volume in 3–5 days (primary lesion). The animals exhibit a decrease in body weight gain during this initial period. Adjuvant arthritis (secondary phase) occurs after a delay of approximately 10 days and is characterized by inflammation of the non-injected sites (right hind leg), decrease in body weight gain and further increases in the volume of the injected hind leg. The compounds of formula I administered in the doses described above beginning on the day of adjuvant injection and continuing for 17 days, thereafter, exclusive of days 4, 5, 11 and 12 protect the animals against development of both primary and secondary lesions of adjuvant arthritis.

The pharmacological profile of the compositions of this invention is further enhanced by the analgesic and antipyretic activity produced by the compounds of formula I at anti-arthritic doses as demonstrated in standard pharmacological test procedures.

The pharmaceutical compositions of this invention are prepared in conventional dosage unit forms by incorporating an amount of a compound of formula I sufficient to produce anti-arthritic activity with a nontoxic pharmaceutical carrier according to accepted procedures. Preferably the compositions will contain an ester derivative of pulvinic acid of formula I in an amount of from about 10 mg. to about 50 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as a ampule or an aqueous or nonaqueous liquid suspension.

The pharmaceutical dosage unit forms described hereinabove exclude simple non-sterile solutions of the active medicament in water or in common organic solvents and exclude simple aqueous suspensions of the active medicament in the absence of a suspending agent.

The method in accordance with this invention comprives administering internally to an animal organism an ester derivative of pulvinic acid of formula I above, usually combined with a pharmaceutical carrier, in an amount sufficient to produce anti-arthritic activity. The active medicament will be administered in a dosage unit, preferably in an amount of from about 10 mg. to about 50 mg. The route of administration may be orally or parenterally, the oral route being preferred. Advantageously equal doses will be administered one to three times daily with the daily dosage regimen being from about 10 mg. to about 150 mg. When the method described above is carried out anti-arthritic activity is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product.

The following examples illustrate the preparation of compounds of formula I and their incorporation into pharmaceutical compositions of this invention, and as such are not to be considered as limiting the invention set forth in the claims appended hereto.

EXAMPLE 1

A mixture of 117.1 g. (1.0m.) of phenylacetonitrile and 326 ml. (2.4m.) of ethyl oxalate is added to an ethanol solution of sodium ethoxide (prepared by dissolving 23.8 g., 1.08m. of sodium in 500 ml. of absolute ethanol) and refluxed two hours. After cooling, diluting with 2500 ml. of water and extracting with ether, the solution is acidified with acetic acid. The solid is removed and washed with water to give ethyl 3-cyano-3-phenylpyruvate, m.p. 127°–129° C.

Ethyl 3-cyano-3-phenylpyruvate (50.0 g., 0.23 m.) and 41.0 g. (0.35 m.) of phenylacetonitrile are added to an alcoholic solution of sodium ethylate [prepared from 13.4 g. (0.58 g. atom) of sodium and 360 ml. of absolute ehtanol] and the resulting yellow solution is refluxed for one and three-quarter hours. The cooled solution is diluted with 700 ml. of water and acidified by slow addition of acetic acid. After further cooling in ice, the suspension is filtered and the removed solid washed with water and dried to give 2,5-diphenyl-3,4-dioxoadiponitrile, m.p. 284°–286° C. (d.).

A mixture of 30.0 g. (0.104 m.) of 2,5-diphenyl-3,4-dioxoadiponitrile in 260 ml. of water, 380 ml. of glacial acetic acid and 190 ml. of concentrated sulfuric acid is refluxed for one hour. The suspension is cooled, poured onto 900 ml. of ice-water and the solid removed and washed to give pulvinic acid, m.p. 215°–216.5° C.

Pulvinic acid (19.0 g., 0.0616 m.) is refluxed in 250 ml. of acetic anhydride for 15 minutes. The cooled solution is stirred into 1200 ml. of ice and water and the oily mass crystallized by stirring in 500 ml. of ethanol. The yellow solid is removed, washed with ethanol and dried to yield pulvinic acid lactone, m.p. 221.5°–223° C.

A mixture of 3.5 g. (0.012 m.) of pulvinic acid lactone in 250 ml. of methanol containing 5 ml. of hydrochloric acid (36%) is refluxed 15 minutes forming a yellow solution. The reaction mixture is concentrated to 50 ml. under reduced pressure, cooled and the crystallized solid, methyl pulvinate, is washed and dried, m.p. 148°–149.5° C.

EXAMPLE 2

Pulvinic acid lactone, 3.3 g., is refluxed in 200 ml. of absolute ethanol containing 5 ml. of hydrochloric acid (36%) for 15 minutes and then evaporated to give the solid ethyl pulvinate, m.p. 124.5°–125.5° C.

EXAMPLE 3

A mixture of 45.3 g. (0.31 m.) of p-chlorophenylacetonitrile and 107 g. (0.72 m., 99 ml.) of diethyl oxalate in an alcoholic sodium ethylate solution [prepared by dissolving 7.13 g. (0.31 g.-atoms) of sodium in 120 ml. of absolute ethanol] is refluxed with stirring for two hours. The cooled reaction mixture is diluted with 700 ml. of water, acidified with acetic acid and cooled to ice bath temperature. The resulting solid is recrystallized from aqueous methanol to give ethyl 3-cyano-3-(p-chlorophenyl)-pyruvate, m.p. 134°–135° C.

Ethyl 3-(p-chlorophenyl)-3-cyanopyruvate (40 g., 0.16 m.) and p-chlorophenylacetonitrile (49.8 g., 0.33 m.) are added to an alcoholic solution of sodium ethylate [prepared from 7.36 g., (0.32 g.-atom) of sodium and 190 ml. of absolute ethanol] and the resulting solution is refluxed for two hours. The reaction mixture is diluted with water, acidified with acetic acid and cooled to ice bath temperature to yield, 2,5-di-(p-chlorophenyl)-3,4-dioxoadiponitrile, m.p. 280° C.

A solution of 15 g. (0.042 m.) of 2,5-di-(p-chlorophenyl)-3,4-dioxoadiponitrile in a mixture of 150 ml. of water, 210 ml. of acetic acid and 105 ml. of concentrated sulfuric acid is stirred and refluxed for two hours. The reaction mixture is diluted with 500 ml. of water and cooled to ice bath temperature to yield 4,4'-dichloropulvinic acid, m.p. 255° C. The acid is refluxed in acetic anhydride to obtain the corresponding 4,4'-dichloropulvinic acid lactone.

A mixture of 5.6 g. (0.0156 m.) of 4,4'-dichloropulvinic acid lactone in 250 ml. of methanol containing 5 ml. of hydrochloric acid is refluxed for 15 minutes. The reaction mixture is concentrated to 50 ml. under reduced pressure, cooled and the crystallized solid removed, washed and dried to give methyl 4,4'-dichloropulvinate, m.p. 175°–177° C.

Similarly, by employing m-chlorophenylacetonitrile in the initial reaction described above to obtain ethyl 3-cyano-3-(m-chlorophenyl)-pyruvate, m.p. 72°–74° C., followed by reaction with m-chlorophenylacetonitrile and the subsequent synthetic steps there is prepared the isomeric product, methyl 3,3'-dichloropulvinate, m.p. 176°–179° C.

EXAMPLE 4

Following the procedures outlined in Examples 1 and 3, p-methoxyphenylacetonitrile is reacted with diethyl oxalate in alcoholic sodium ethoxide solution to give ethyl 3-cyano-3-(p-methoxyphenyl)-pyruvate which is then similarly reacted with phenylacetonitrile to yield 2-(p-methoxyphenyl)-5-phenyl-3,4-dioxoadiponitrile, m.p. 256°–258° C.

A solution of the adiponitrile in water, acetic acid and concentrated sulfuric acid is refluxed for two hours and the resulting crude mixture of 4- and 4'-methoxypulvinic acid is refluxed in acetic anhydride to give 4-methoxypulvinic acid lactone, 204°–208° C.

A mixture of 4.0 g. of 4-methoxypulvinic acid lactone and 500 ml. of methanol containing 6 ml. of hydrochloric acid (36%) is refluxed until a clear solution forms. The solution is evaporated to dryness and the solid is boiled in acetone and cooled to give methyl 4'-methoxypulvinate, m.p. 200°–202° C.

The acetone filtrate is evaporated to a dark oil which is stirred in ice-cold acetone until a thick solid forms. This is filtered to yield methyl 4-methoxypulvinate, m.p. 117°–119° C.

Similarly, by employing (m-bromo-p-methoxyphenyl)-acetonitrile in the initial reaction described above to obtain ethyl 3-cyano-3-(m-bromo-p-methoxyphenyl)-pyruvate followed by reaction with phenylacetonitrile and the subsequent synthetic steps there are prepared methyl 3'-bromo-4'-methoxypulvinate and methyl 3-bromo-4-methoxypulvinate.

EXAMPLE 5

Following the procedures outlined in Examples 1 and 3, p-methylphenylacetonitrile and diethyl oxalate are reacted in alcoholic sodium ethoxide to obtain ethyl 3-cyano-3-(p-methylphenyl)-pyruvate, m.p. 86°–88° C. The latter is reacted with p-methylphenylacetonitrile to give 2,5-di-(p-methylphenyl)-3,4-dioxoadiponitrile, m.p. 270°–272° C.

The adiponitrile is refluxed with water, acetic acid and concentrated sulfuric acid to give 4,4'-dimethylpulvinic acid, m.p. 246°–250° C., which is refluxed in turn with acetic anhydride to yield 4,4'-dimethylpulvinic acid lactone. The lactone is ring opened with methanol and hydrochloric acid to the product, methyl 4,4'-dimethylpulvinate, m.p. 187°–189° C.

Similarly, employing (2-methoxy-5-methylphenyl)-acetonitrile as the reactant above there results as the final product, methyl 2,2'-dimethoxy-5,5'-dimethylpulvinate.

EXAMPLE 6

By employing the procedures set forth in Examples 1 and 3, p-fluorophenylacetonitrile is reacted with diethyl oxalate in alcoholic sodium ethoxide to give ethyl 3-cyano-3-(p-fluorophenyl)-pyruvate. Reaction of the latter under similar conditions with p-fluorophenylacetonitrile results in 2,5-di-(p-fluorophenyl)-3,4-dioxoadiponitrile.

The adiponitrile is refluxed in water, acetic acid and concentrated sulfuric acid to yield 4,4'-difluoropulvinic acid which is treated with acetic anhydride to obtain 4,4'-difluoropulvinic acid lactone. The lactone ring is opened with methanol and hydrochloric acid to give methyl 4,4'-difluoropulvinate, m.p. 151° C.

Similarly, by utilizing m-trifluoromethylphenylacetonitrile or (m-chloro-p-fluorophenyl)- acetonitrile as the initial reactants as described above there are ultimately produced methyl 3,3'-bistrifluoromethylpulvinate, m.p. 144° C., and methyl 3,3'-dichloro-4,4'-difluoropulvinate, respectively.

EXAMPLE 7

As described in Example 1, ethyl 3-cyano-3-phenylpyruvate is reacted with 3,4,5-trimethyoxyphenylacetonitrile in an alcoholic solution of sodium ethoxide to give 2-(3',4',5'-trimethoxyphenyl)-5-phenyl-3,4-dioxoadiponitrile. The latter is refluxed in a mixture of water, glacial acetic acid and concentrated sulfuric acid to give a mixture of 3,4,5- and 3',4',5'-trimethoxypulvinic acid which is then refluxed in acetic anhydride to result in the formation of 3,4,5-trimethoxypulvinic acid lactone.

A mixture of 8.7 g. of 3,4,5-trimethoxypulvinic acid lactone and 700 ml. of methanol containing 12 ml. of hydrochloric acid (36%) is refluxed for two hours to form a clear solution, and then cooled to precipitate methyl 3,4,5-trimethoxypulvinate, m.p. 209°–211° C.

The filtrate is evaporated to dryness and the residue is dissolved in 500 ml. of hot methanol, cooled and the solid which precipitates is filtered (a mixture of both isomers). The filtrate is allowed to sit for one-half hour and the yellow solid which forms is collected to give methyl 3',4',5'-trimethoxypulvinate, m.p. 170°–172° C.

EXAMPLE 8

By following the procedures outlined in Examples 1 and 3,3,4-dimethoxyphenylacetonitrile is reacted with diethyl oxalate in alcoholic sodium ethoxide solution to give ethyl 3-cyano-3-(3',4'-dimethoxyphenyl)-pyruvate, m.p. 139°–140° C. This compound is similarly reacted with 3,4-dimethoxyphenylacetonitrile which results in the formation of 2,5-di-(3',4'-dimethoxyphenyl)-3,4-dioxoadiponitrile. The latter is refluxed with water, acetic acid and sulfuric acid to obtain 3,4,3',4'-tetramethoxypulvinic acid, 285° C., which is treated with acetic anhydride to give the corresponding acid lactone.

3,4,3',4'-Tetramethoxypulvinic acid lactone (4.0 g.) is dissolved in 2% absolute methanolic potassium hydroxide (700 ml.) and set aside for 30 minutes at room temperature, then diluted with 700 ml. of water and acidified with hydrochloric acid. The yellow solid that separates is treated with aqueous sodium hydrogen carbonate and filtered again. The filtrate is acidified and the solid removed, washed and dried to give methyl 3,4,3', 4'-tetramethoxypulvinate, m.p. 195°–196° C.

Similarly, by employing p-methoxyphenylacetonitrile or m-methoxyphenylacetonitrile as the initial reactants as described above there are obtained as final products, methyl 4,4'-dimethoxypulvinate, m.p. 177°–178° C. and methyl 3,3'-dimethoxypulvinate, m.p. 154°–157° C., respectively.

| EXAMPLE 9 Ingredients | Mg./Tablet |
| --- | --- |
| Methyl pulvinate | 10 |
| Calcium sulfate, dihydrate | 150 |
| Sucrose | 25 |
| Starch | 15 |
| Talc | 5 |
| Stearic Acid | 3 |

The sucrose, calcium sulfate and methyl pulvinate are thoroughly mixed and granulated with hot 10% gelatin solution. The wetted mass is passed through a No. 6 mesh screen directly onto drying trays. The granules are dried at 120° F. and passed through a No. 20 mesh screen, mixed with the starch, talc and stearic acid, and compressed into tablets.

| EXAMPLE 10 Ingredients | Mg./Capsule |
| --- | --- |
| Methyl pulvinate | 50 |
| Magnesium stearate | 5 |
| Lactose | 350 |

The above ingredients are screened through a No. 40 mesh screen, mixed and filled into No. 0 hard gelatin capsules.

EXAMPLE 11

To a solution of 6.6 g. (0.044 m.) of p-chlorophenylacetonitrile and 20 ml. of dry glyme is added 6.2 g. (0.13 m.) of sodium hydride (50% in oil). Ethyl 3-cyano-3-phenylpyruvate, 9.55 g. (0.044 m.) is added in portions at −10° C. and then the mixture is stirred at room temperature overnight. The reaction mixture is diluted with 150 ml. of water, extracted with ether, acidified with 15 ml. of acetic acid and the solid is filtered to yield 2-(p-chlorophenyl)-5-phenyl-3,4-dioxoadiponitrile, m.p. 210° C. (dec.).

A solution of the adiponitrile in water, acetic acid and concentrated sulfuric acid is refluxed for two hours and the resulting crude mixture of 4- and 4'-chloropulvinic acid is refluxed in acetic anhydride to give 4-chloropulvinic acid lactone, m.p. 213°–214° C.

A mixture of 9.0 g. of 4-chloropulvinic acid lactone in 500 ml. of methanol containing 15 ml. of hydrochloric acid (36%) is refluxed for 15 minutes. The clear reaction mixture is cooled slowly to give methyl 4'-chloropulvinate, m.p. 155°–200° C.

Similarly, by employing m,p-dichlorophenylacetonitrile in the initial reaction described above to obtain 2-(m,p-dichlorophenyl-5-phenyl-3,4-dioxoadiponitrile followed by the subsequent synthetic steps there is prepared 3,4-dichloropulvinic acid lactone. The latter, 12.5 g. (0.035 m.), is dissolved in a solution of 48 g. of potassium hydroxide in 1500 ml. of methanol. After standing for one hour at room temperature the solution is acidified with hydrochloric acid and diluted with water to separate methyl 3',4'-dichloropulvinate, m.p. 162.5°–164° C.

EXAMPLE 12

Following the procedures of Examples 1 and 3, 2-(p-methylphenyl)-5-phenyl-3,4-dioxoadiponitrile (m.p. 255°–256° C.) is refluxed with water, acetic acid and concentrated sulfuric acid to give a crude mixture of 4- and 4'-methylpulvinic acid. The latter is refluxed in acetic anhydride to give 4-methylpulvinic acid lactone, m.p. 211°–213° C.

A mixture of 7.4 g. (0.02 m.) of 4-methylpulvinic acid lactone and 500 ml. of methanol containing 15 ml. of hydrochloric acid (36%) is refluxed for two hours. After cooling and diluting with water the mixture is recrystallized from methanol to yield methyl 4-methylpulvinate, m.p. 153°–155° C., and from the filtrate methyl 4'-methylpulvinate, m.p. 136°–138° C.

EXAMPLE 13

A solution of 3.2 g. (0.01 m.) of methyl pulvinate and 1.6 ml. (4.7 g, 0.03 m.) of bromine in 50 ml. of chloroform is allowed to stand overnight at room temperature. The excess bromine is removed by washing with sodium thiosulfate solution and the chloroform solution is concentrated to separate methyl 4'-bromopulvinate, m.p. 167.5°–169° C.

EXAMPLE 14

Following the procedures outlined in Examples 1 and 3, 3,4-methylenedioxyphenylacetonitrile is reacted with diethyl oxalate in alcoholic sodium ethoxide solution to give ethyl 3-cyano-3-(3',4'-methylenedioxyphenyl)-pyruvate which is reacted with phenylacetonitrile to yield 2-(3',4'-methylenedioxyphenyl)-5-phenyl-3,4-dioxoadiponitrile.

A solution of the adiponitrile in water, acetic acid and concentrated sulfuric acid is refluxed for two hours and the resulting crude mixture of 3,4- and 3',4'-methylenedioxypulvinic acid is refluxed in acetic anhydride to give 3,4-methylenedioxypulvinic acid lactone.

The lactone, 10.0 g., is stirred in a solution of 40 g. of potassium hydroxide in 1 l. of methanol at about 10° C. for one hour, diluted with 700 ml. of water, filtered and then acidified. The solid is dissolved in about 100 ml. of chloroform and chromatographed, eluting with chloroform. The eluate is evaporated to give, after recrystallization from methanol-acetone, methyl 3',4'-methylenedioxypulvinate, m.p. 191.5°–192.5° C.

The filtrates from recrystallization were evaporated and the solid is dissolved in methanol containing sodium methoxide, cooled and filtered to remove 3',4'-isomer. The filtrate is acidified to give the 3,4-isomer which is again dissolved in methanol containing sodium methoxide and filtered. This filtrate is acidified with 10% hydrochloric acid and filtered, washed with water and dried to yield pure methyl 3,4-methylenedioxypulvinate, m.p. 157°–160° C.

EXAMPLE 15

By reacting ethyl 3-cyano-3-(3',4'-methylenedioxyphenyl)-pyruvate with 3,4-methylenedioxyphenylacetonitrile following procedures set forth in Examples 1 and 3 there is obtained 2,5-di-(3',4'-methylenedioxyphenyl)-3,4-dioxoadiponitrile.

The adiponitrile is refluxed in water, acetic acid and concentrated sulfuric acid to yield 3,4,3',4'-bismethylenedioxypulvinic acid which is treated with acetic anhydride to give 3,4,3',4'-bismethylenedioxypulvinic acid lactone.

A mixture of 3.78 g. (0.01 m.) of the above lactone in 410 ml. of 2% methanolic potassium hydroxide is stirred at room temperature for four hours, filtered and the filtrate acidified with hydrochloric acid. The solid filtered from this is treated with sodium bicarbonate and the soluble material is again acidified to yield methyl 3,4,3',4'-bismethylenedioxypulvinate, m.p. 178°–180° C.

EXAMPLE 16

As described in Example 1, ethyl 3-cyano-3-phenyl-pyruvate is reacted with p-methylthiophenylacetonitrile in an alcoholic solution of sodium ethoxide to give 2-(p-methylthiophenyl)-5-phenyl-3,4-dioxoadiponitrile. The latter is refluxed in a mixture of water, glacial acetic acid and concentrated sulfuric acid to give a mixture of 4- and 4'-methylthiopulvinic acid which is then refluxed in acetic anhydride to result in the formation of 4-methylthiopulvinic acid lactone.

A mixture of 6.0 g. of the above lactone in a solution of 24.0 g. of potassium hydroxide in 750 ml. of methanol is allowed to stand at room temperature for one-half hour, diluted with 700 ml. of water and then acidified with concentrated hydrochloric acid. The solid is filtered, washed with water, dried and recrystallized from methanol-acetone. A second recrystallization gives methyl 4-methylthiopulvinate, m.p. 147.5°–150° C.

All the filtrates are combined, concentrated and cooled to give methyl 4'-methylthiopulvinate, m.p. 149°–150.5° C.

EXAMPLE 17

To a cold solution (−10° C.) of 2.07 g. of methyl 4-methylthiopulvinate in 30 ml. of chloroform is added a cold solution of 1.11 g. of m-chloroperbenzoic acid in 25 ml. of chloroform, dropwise over about 15 minutes. The resulting solution is stirred in the cold for one-half hour and then evaporated in vacuo. The residue is taken up in methanolacetone, filtered, concentrated and cooled to yield methyl 4-methylsulfinylpulvinate, m.p. 213°–215° C. (dec.).

Similarly, methyl 4'-methylthiopulvinate is reacted as described above to furnish methyl 4'-methylsulfinylpulvinate, m.p. 184°–185° C.

EXAMPLE 18

By following the procedures outlined in Examples 1 and 3, p-methylthiophenylacetonitrile is reacted with diethyl oxalate in alcoholic sodium ethoxide solution to give ethyl 3-cyano-3-(p-methylthiophenyl)-pyruvate. This compound is similarly reacted with p-methylthiophenylacetonitrile which results in the formation of 2,5-di-(p-methylthiophenyl)-3,4-dioxoadiponitrile.

The latter is refluxed with water, acetic acid and sulfuric acid to obtain 4,4'-dimethylthiopulvinic acid which is treated with acetic anhydride to give the corresponding acid lactone.

4,4'-Dimethylthiopulvinic acid lactone (3.5 g.) is dissolved in 700 ml. of methanol containing 14.0 g. of potassium hydroxide and stirred for one hour at room temperature. The mixture is cooled by adding 200 ml. of ice water and then acidified with cold dilute hydrochloric acid to precipitate methyl 4,4'-dimethylthiopulvinate, m.p. 173°–174° C.

EXAMPLE 19

Following the procedures of Example 4 and employing p-ethyoxyphenylacetonitrile as the initial reactant there is obtained 4-ethoxypulvinic acid lactone. The latter (9.0 g.) is added to a solution of 36.0 g. of potassium hydroxide in 900 ml. of methanol and the mixture is allowed to stand at room temperature for one-half hour. The reaction mixture is diluted with about 600 ml. of water, filtered and acidified with concentrated hydrochloric acid. The oily solid is recrystallized from methanol-acetone to give a mixture of methyl 4- and 4'-ethoxypulvinate. The mixture is dissolved in methanol containing sodium methoxide to fractionally crystallize pure methyl 4'-ethoxypulvinate, m.p. 151°–152° C.

EXAMPLE 20

To a solution of 40.0 g. of potassium hydroxide in 1200 ml. of methanol is added 10.5 g. of 4-ethoxypulvinic acid lactone and the mixture is stirred at room temperature for one and one-half hours. This mixture is cooled, diluted with about 600 ml. of water and acidified with hydrochloric acid. The oily solid is filtered, washed with water, dried and dissolved in 60 ml. of hot acetone. Cooling precipitates pure methyl 4-ethoxypulvinate, m.p. 153°–154° C.

EXAMPLE 21

Following the procedures outlined in Example 4 and employing m-methoxyphenylacetonitrile as the initial reactant there is obtained 3-methoxypulvinic acid lactone. The latter (10.0 g.) is added to a solution of 40.0 g. of potassium hydroxide dissolved in 1 l. of methanol, cooled to −50° C. The resulting mixture is stirred at −50° to −25° C. for about two and one-half hours, diluted with water and warmed to about 15° C. The filtered solution is acidified with hydrochloric hydrochloric acid and the filtered solid is washed with water. The dried solid is recrystallized from methanol-acetone to give methyl 3′-methoxypulvinate, m.p. 168°–170° C.

Similarly, by employing (m-chloro-p-methoxyphenyl)-acetonitrile or (2-chloro-5-methylphenyl)-acetonitrile as the initial reactants as described above these are obtained as final products, methyl 3′-chloro-4′-methoxypulvinate and methyl 2′-chloro-5′-methylpulvinate, respectively.

EXAMPLE 22

Following the procedures of Example 4 and employing o-methoxyphenylacetonitrile as the initial reactant there is obtained 2-methoxypulvinic acid lactone. The latter (6.0 g.) is added to a solution of 24.0 g. of potassium hydroxide in 1200 ml. of methanol, stirred and allowed to stand at room temperature for one hour. The resulting solution is diluted with water, acidified with hydrochloric acid and the solid filtered to give a mixture of methyl 2- and 2′-methoxypulvinate.

The mixture is recrystallized from methanol-acetone to give pure methyl 2-methoxypulvinate, m.p. 155.5°–157° C. The filtrate is evaporated to dryness, taken up in benzene and then cyclohexane is added to precipitate methyl 2′-methoxypulvinate, m.p. 131.5°–133° C.

EXAMPLE 23

Following the procedures of Example 4 and employing p-n-butoxyphenylacetonitrile as the initial reactant there is obtained 4-n-butoxypulvinic acid lactone. The latter (8.0 g.) is added to a cooled solution of 32.0 g. of potassium hydroxide in 800 ml. of methanol. After stirring for one-half hour the mixture is diluted with 600 ml. of water and acidified to form an oil. The oil is slurried in water and dried to give a glass which is taken up in methanol-acetone. This solution is cooled and the solid precipitate is fractionally recrystallized to give methyl 4-n-butoxypulvinate, m.p. 103°–105° C.

A fraction which is a mixture of 4- and 4′-isomers is placed in a solution of 0.5 g. of sodium methoxide in about 50 ml. of methanol and heated to dissolution. Cooling precipitates a solid which is filtered, washed with methanol containing a small amount of 10% hydrochloric acid and dried to give methyl 4′-n-butoxypulvinate, m.p. 101°–104° C.

Similarly, by employing (m-chloro-methylphenyl)-acetonitrile as the reactant in the above synthetic sequence there are obtained as final products, methyl 3-chloro-2-methylpulvinate and methyl 3′-chloro-2′-methylpulvinate.

What is claimed is:

1. A chemical compound of the formula:

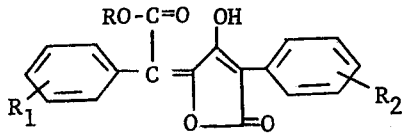

in which:
R is methyl or ethyl; and
$R_1$ and $R_2$ are substituents selected as follows so that for a given $R_1$ in column 1 the corresponding $R_2$ is in the adjacent position of column 2:

| $R_1$ | $R_2$ |
|---|---|
| hydrogen | 3-bromo-4-methoxy |
| 3-bromo-4-methoxy | hydrogen |
| 2-methoxy-5 methyl | 2-methoxy-5-methyl |
| 3-chloro-4-fluoro | 3-chloro-4-fluoro |
| hydrogen | 3,4-dichloro |
| 4-methylthio | hydrogen |
| hydrogen | 4-methylthio |
| 4-methylsulfinyl | hydrogen |
| hydrogen | 4-methylsulfinyl |
| 4-methylthio | 4-methylthio |
| hydrogen | 3-chloro-4-methoxy |
| hydrogen | 2-chloro-5-methyl |
| 3-chloro-2-methyl | hydrogen |
| hydrogen | 3-chloro-2-methyl. |

2. A chemical compound according to claim 1 in which R is methyl and $R_1$ is hydrogen.

3. A chemical compound according to claim 2 in which $R_2$ is methylthio.

4. A chemical compound according to claim 2 in which $R_2$ is methylsulfinyl.

5. A chemical compound according to claim 1 in which R is methyl and $R_1$ and $R_2$ are each methylthio.

* * * * *

UNITED STATES PATENT AND TRADEMARK OFFICE
CERTIFICATE OF CORRECTION

PATENT NO. : 3,944,571
DATED : March 16, 1976
INVENTOR(S) : Blaine M. Sutton, Donald T. Walz and James W. Wilson It is certified that error appears in the above–identified patent and that said Letters Patent are hereby corrected as shown below:

Column 12, line 50, should read "is 4-methylthio."

Column 12, line 52, should read "is 4-methylsulfinyl."

Column 12, line 54, should read "each 4-methylthio."

Signed and Sealed this eighteenth Day of May 1976

[SEAL]

Attest:

RUTH C. MASON
*Attesting Officer*

C. MARSHALL DANN
*Commissioner of Patents and Trademarks*